(12) United States Patent
Doron et al.

(10) Patent No.: US 8,744,580 B2
(45) Date of Patent: *Jun. 3, 2014

(54) IMPLANTABLE MEDICAL DEVICE WITH INTEGRATED ACOUSTIC TRANSDUCER

(75) Inventors: Eyal Doron, Kiriat-Yam (IL); Abraham Penner, Tel Aviv (IL)

(73) Assignee: Remon Medical Technologies, Ltd., Caesarea (IL)

( * ) Notice: Subject to any disclaimer, the term of this patent is extended or adjusted under 35 U.S.C. 154(b) by 430 days.

This patent is subject to a terminal disclaimer.

(21) Appl. No.: 12/504,946

(22) Filed: Jul. 17, 2009

(65) Prior Publication Data

US 2010/0004718 A1    Jan. 7, 2010

Related U.S. Application Data

(63) Continuation of application No. 11/287,557, filed on Nov. 23, 2005, now Pat. No. 7,580,750.

(60) Provisional application No. 60/630,801, filed on Nov. 24, 2004.

(51) Int. Cl.
*A61N 1/00* (2006.01)

(52) U.S. Cl.
USPC .............................. 607/32; 607/60; 367/140

(58) Field of Classification Search
CPC ........... A61N 1/37211; A61N 1/37217; A61N 1/37223; A61N 1/37288; A61N 1/3758
USPC .............. 607/6, 30, 32, 36, 60; 367/180, 140, 367/157, 165, 173, 174
See application file for complete search history.

(56) References Cited

U.S. PATENT DOCUMENTS

| | | |
|---|---|---|
| 2,967,957 A | 1/1961 | Massa |
| 3,568,661 A | 3/1971 | Franklin |
| 3,676,720 A | 7/1972 | Libby et al. |
| 3,757,770 A | 9/1973 | Brayshaw et al. |
| 3,792,204 A | 2/1974 | Murayama et al. |
| 3,798,473 A | 3/1974 | Murayama et al. |
| 3,832,580 A | 8/1974 | Yamamuro et al. |
| 3,894,198 A | 7/1975 | Murayama et al. |
| 3,940,637 A | 2/1976 | Ohigashi et al. |
| 3,978,353 A | 8/1976 | Kinoshita |
| 4,008,408 A | 2/1977 | Kodama |

(Continued)

FOREIGN PATENT DOCUMENTS

| | | |
|---|---|---|
| DE | 1101331 | 4/1958 |
| DE | 3222349 | 1/1984 |

(Continued)

OTHER PUBLICATIONS

Blevins Ph.D. "Formulas for Natural Frequency and Mode Shape" Floriday 1979; p. 240; ISBN: 1575241846.

(Continued)

*Primary Examiner* — Scott Getzow
(74) *Attorney, Agent, or Firm* — Faegre Baker Daniels LLP

(57) ABSTRACT

An implantable medical device comprises a hermetically sealed housing having a housing wall with an interior surface, and an ultrasonic acoustic transducer, the transducer comprising one or more piezoelectric discs fixed to the interior surface of the housing wall, such that the housing wall acts as a diaphragm in response to induced movement by the one or more piezoelectric material discs.

19 Claims, 6 Drawing Sheets

(56) References Cited

U.S. PATENT DOCUMENTS

| | | |
|---|---|---|
| 4,051,455 A | 9/1977 | Fowler |
| 4,056,742 A | 11/1977 | Tibbetts |
| 4,064,375 A | 12/1977 | Russell et al. |
| 4,096,756 A | 6/1978 | Alphonse |
| 4,127,110 A | 11/1978 | Bullara |
| 4,170,742 A | 10/1979 | Itagaki et al. |
| 4,181,864 A | 1/1980 | Etzold |
| 4,227,407 A | 10/1980 | Drost |
| 4,281,484 A | 8/1981 | Massa |
| 4,431,873 A | 2/1984 | Dunn et al. |
| 4,433,400 A | 2/1984 | De Reggi et al. |
| 4,440,983 A | 4/1984 | Facoetti et al. |
| 4,456,850 A | 6/1984 | Inoue et al. |
| 4,471,786 A | 9/1984 | Inagaki et al. |
| 4,481,950 A | 11/1984 | Duggan |
| 4,517,665 A | 5/1985 | De Reggi et al. |
| 4,519,401 A | 5/1985 | Ko et al. |
| 4,541,431 A | 9/1985 | Ibrahim et al. |
| 4,558,249 A | 12/1985 | Lerch et al. |
| 4,577,132 A | 3/1986 | Ohigashi et al. |
| 4,580,074 A | 4/1986 | Gilman |
| 4,593,703 A | 6/1986 | Cosman |
| 4,600,855 A | 7/1986 | Strachan |
| 4,642,508 A | 2/1987 | Suzuki et al. |
| 4,653,036 A | 3/1987 | Harris et al. |
| 4,653,508 A | 3/1987 | Cosman |
| 4,660,568 A | 4/1987 | Cosman |
| 4,672,976 A | 6/1987 | Kroll |
| 4,676,255 A | 6/1987 | Cosman |
| 4,677,337 A | 6/1987 | Kleinschmidt et al. |
| 4,781,715 A | 11/1988 | Wurzel |
| 4,793,825 A | 12/1988 | Benjamin et al. |
| 4,835,435 A | 5/1989 | Yeung et al. |
| 4,846,191 A | 7/1989 | Brockway et al. |
| 4,911,172 A | 3/1990 | Bui et al. |
| 4,940,052 A | 7/1990 | Mann et al. |
| 4,958,100 A | 9/1990 | Crawley et al. |
| 4,992,692 A | 2/1991 | Dias |
| 5,012,815 A | 5/1991 | Bennett, Jr. et al. |
| 5,024,224 A | 6/1991 | Engebretson |
| 5,088,576 A | 2/1992 | Potthoff et al. |
| 5,113,859 A * | 5/1992 | Funke ............... 607/4 |
| 5,160,870 A | 11/1992 | Carson et al. |
| 5,178,153 A | 1/1993 | Einzig |
| 5,283,397 A | 2/1994 | Pavlovic |
| 5,289,821 A | 3/1994 | Swartz |
| 5,300,875 A | 4/1994 | Tuttle |
| 5,304,206 A | 4/1994 | Baker, Jr. et al. |
| 5,314,457 A | 5/1994 | Jeutter et al. |
| 5,339,290 A | 8/1994 | Greenstein |
| 5,367,500 A | 11/1994 | Ng |
| 5,381,067 A | 1/1995 | Greenstein et al. |
| 5,381,386 A | 1/1995 | Lum et al. |
| 5,410,587 A | 4/1995 | Grunwell |
| 5,411,551 A | 5/1995 | Winston et al. |
| 5,423,334 A | 6/1995 | Jordan |
| 5,438,553 A | 8/1995 | Wilson et al. |
| 5,476,488 A | 12/1995 | Morgan et al. |
| 5,483,501 A | 1/1996 | Park et al. |
| 5,488,954 A | 2/1996 | Sleva et al. |
| 5,495,137 A | 2/1996 | Park et al. |
| 5,507,786 A | 4/1996 | Morgan et al. |
| 5,554,177 A | 9/1996 | Kieval et al. |
| 5,562,714 A | 10/1996 | Grevious |
| 5,571,152 A | 11/1996 | Chen et al. |
| 5,628,782 A | 5/1997 | Myers |
| 5,679,026 A | 10/1997 | Fain et al. |
| 5,704,352 A | 1/1998 | Tremblay et al. |
| 5,733,313 A | 3/1998 | Barreras, Sr. et al. |
| 5,735,887 A | 4/1998 | Barreras, Sr. et al. |
| 5,741,316 A | 4/1998 | Chen et al. |
| 5,749,909 A | 5/1998 | Schroeppel et al. |
| 5,757,104 A | 5/1998 | Getman et al. |
| 5,776,178 A | 7/1998 | Pohndorf et al. |
| 5,792,195 A | 8/1998 | Carlson et al. |
| 5,807,258 A | 9/1998 | Cimochowski et al. |
| 5,825,117 A | 10/1998 | Ossmann et al. |
| 5,832,924 A | 11/1998 | Archibald et al. |
| 5,833,603 A | 11/1998 | Kovacs et al. |
| 5,843,135 A | 12/1998 | Weijand et al. |
| 5,870,351 A | 2/1999 | Ladabaum et al. |
| 5,873,835 A | 2/1999 | Hastings et al. |
| 5,879,283 A | 3/1999 | Adams et al. |
| 5,935,081 A | 8/1999 | Kadhiresan |
| 5,956,292 A | 9/1999 | Bernstein |
| 5,957,950 A | 9/1999 | Mockros et al. |
| 5,967,986 A | 10/1999 | Cimochowski et al. |
| 6,044,298 A | 3/2000 | Salo et al. |
| 6,053,873 A | 4/2000 | Govari et al. |
| 6,058,329 A | 5/2000 | Salo et al. |
| 6,068,589 A | 5/2000 | Neukermans |
| 6,082,367 A | 7/2000 | Greeninger et al. |
| 6,140,740 A | 10/2000 | Porat et al. |
| 6,141,588 A | 10/2000 | Cox et al. |
| 6,185,452 B1 | 2/2001 | Schulman et al. |
| 6,223,081 B1 | 4/2001 | Kerver |
| 6,353,277 B1 | 3/2002 | Hahn-Jose |
| 6,409,675 B1 | 6/2002 | Turcott |
| 6,475,170 B1 | 11/2002 | Doron et al. |
| 6,477,406 B1 * | 11/2002 | Turcott ............... 600/518 |
| 6,480,733 B1 | 11/2002 | Turcott |
| 6,486,588 B2 | 11/2002 | Doron et al. |
| 6,504,286 B1 | 1/2003 | Porat et al. |
| 6,504,289 B2 | 1/2003 | Toda et al. |
| 6,527,729 B1 | 3/2003 | Turcott |
| 6,537,200 B2 | 3/2003 | Leysieffer et al. |
| 6,554,761 B1 * | 4/2003 | Puria et al. ............... 600/25 |
| 6,575,894 B2 | 6/2003 | Leysieffer et al. |
| 6,600,949 B1 | 7/2003 | Turcott |
| 6,628,989 B1 | 9/2003 | Penner et al. |
| 6,629,922 B1 | 10/2003 | Puria et al. |
| 6,629,951 B2 | 10/2003 | Laufer et al. |
| 6,643,548 B1 | 11/2003 | Mai et al. |
| 6,645,145 B1 | 11/2003 | Dreschel et al. |
| 6,654,638 B1 | 11/2003 | Sweeney |
| 6,671,550 B2 | 12/2003 | Iaizzo et al. |
| 6,697,674 B2 | 2/2004 | Leysieffer |
| 6,720,709 B2 | 4/2004 | Porat et al. |
| 6,740,076 B2 | 5/2004 | Hoben et al. |
| 6,741,714 B2 | 5/2004 | Jensen |
| 6,763,722 B2 | 7/2004 | Fjield et al. |
| 6,764,446 B2 | 7/2004 | Wolinsky et al. |
| 6,772,490 B2 | 8/2004 | Toda |
| 6,792,308 B2 | 9/2004 | Corbucci |
| 6,999,685 B1 | 2/2006 | Kawase et al. |
| 7,015,392 B1 | 3/2006 | Dickenson |
| 7,016,739 B2 | 3/2006 | Bange et al. |
| 7,024,248 B2 | 4/2006 | Penner et al. |
| 7,035,684 B2 | 4/2006 | Lee |
| 7,107,103 B2 | 9/2006 | Schulman et al. |
| 7,114,502 B2 | 10/2006 | Schulman et al. |
| 7,115,096 B2 | 10/2006 | Siejko et al. |
| 7,118,531 B2 | 10/2006 | Krill |
| 7,123,962 B2 | 10/2006 | Siejko et al. |
| 7,127,290 B2 | 10/2006 | Girouard et al. |
| 7,176,602 B2 | 2/2007 | Schlenke |
| 7,198,603 B2 | 4/2007 | Penner et al. |
| 7,220,232 B2 | 5/2007 | Suorsa et al. |
| 7,228,175 B2 | 6/2007 | Jain et al. |
| 7,236,821 B2 | 6/2007 | Cates |
| 7,248,923 B2 | 7/2007 | Maile et al. |
| 7,260,429 B2 | 8/2007 | Siejko et al. |
| 7,273,457 B2 | 9/2007 | Penner |
| 7,283,874 B2 | 10/2007 | Penner |
| 7,335,169 B2 | 2/2008 | Thompson et al. |
| 7,431,699 B2 | 10/2008 | Siejko et al. |
| 7,522,962 B2 | 4/2009 | Doron et al. |
| 7,634,318 B2 | 12/2009 | Tran et al. |
| 8,277,441 B2 | 10/2012 | Porat et al. |
| 8,340,778 B2 | 12/2012 | Tran et al. |
| 2001/0026111 A1 | 10/2001 | Doran et al. |
| 2002/0045921 A1 | 4/2002 | Wolinsky et al. |
| 2002/0062143 A1 | 5/2002 | Baudino et al. |
| 2002/0177782 A1 | 11/2002 | Penner |

(56) References Cited

U.S. PATENT DOCUMENTS

| | | |
|---|---|---|
| 2003/0006673 A1 | 1/2003 | Porat et al. |
| 2003/0014080 A1 | 1/2003 | Baudino |
| 2003/0036746 A1 | 2/2003 | Penner et al. |
| 2004/0106954 A1 | 6/2004 | Whitehurst et al. |
| 2004/0122484 A1 | 6/2004 | Hatlestad et al. |
| 2004/0127792 A1 | 7/2004 | Siejko et al. |
| 2004/0138572 A1 | 7/2004 | Thiagarajan |
| 2004/0172079 A1 | 9/2004 | Chinchoy |
| 2004/0204744 A1 | 10/2004 | Penner |
| 2004/0230249 A1 | 11/2004 | Haefner |
| 2004/0260214 A1 | 12/2004 | Echt et al. |
| 2005/0131472 A1 | 6/2005 | Ding et al. |
| 2005/0137490 A1 | 6/2005 | Scheiner et al. |
| 2005/0149138 A1 | 7/2005 | Min et al. |
| 2006/0004290 A1 | 1/2006 | Smith et al. |
| 2006/0009818 A1 | 1/2006 | Von Arx et al. |
| 2006/0136004 A1 | 6/2006 | Cowan |
| 2006/0142819 A1 | 6/2006 | Penner et al. |
| 2006/0149329 A1 | 7/2006 | Penner |
| 2007/0049977 A1 | 3/2007 | Von Arx et al. |
| 2007/0055184 A1 | 3/2007 | Echt et al. |
| 2007/0093875 A1 | 4/2007 | Chavan et al. |
| 2007/0142728 A1 | 6/2007 | Penner |
| 2008/0015413 A1 | 1/2008 | Barlow et al. |
| 2008/0021289 A1 | 1/2008 | Zhang et al. |
| 2008/0021509 A1 | 1/2008 | Mi et al. |
| 2008/0021510 A1 | 1/2008 | Mi et al. |
| 2008/0033497 A1 | 2/2008 | Bulkes et al. |
| 2008/0195186 A1 | 8/2008 | Li et al. |
| 2008/0294208 A1 | 11/2008 | Willis et al. |
| 2010/0049269 A1 | 2/2010 | Tran |
| 2010/0094105 A1 | 4/2010 | Porat et al. |
| 2012/0327747 A1 | 12/2012 | Porat et al. |

FOREIGN PATENT DOCUMENTS

| | | |
|---|---|---|
| EP | 0897690 | 8/1997 |
| EP | 0798016 | 10/1997 |
| EP | 1151719 | 4/2001 |
| EP | 1422970 | 5/2004 |
| JP | 57177735 | 11/1982 |
| JP | 60-216697 | 10/1985 |
| JP | 62-073900 | 4/1987 |
| JP | 62102734 | 5/1987 |
| JP | 05023323 | 2/1993 |
| JP | 05-284599 | 10/1993 |
| JP | 07-046694 | 2/1995 |
| JP | 07-301670 | 11/1995 |
| JP | 09-225042 | 9/1997 |
| JP | 09237398 | 9/1997 |
| JP | 10-294995 | 11/1998 |
| JP | 2000-334048 | 12/2000 |
| JP | 2001-514455 | 9/2001 |
| JP | 2002-508682 | 3/2002 |
| JP | 2002-528887 | 9/2002 |
| JP | 2003-079621 | 3/2003 |
| JP | 2003-519542 | 6/2003 |
| JP | 2003-218805 | 7/2003 |
| JP | 2004-147319 | 5/2004 |
| JP | 2006-015137 | 1/2006 |
| JP | 2006-166985 | 6/2006 |
| RU | 2239383 | 11/2004 |
| WO | WO83/03345 | 10/1983 |
| WO | WO97/01986 | 1/1997 |
| WO | WO97/33513 | 9/1997 |
| WO | WO97/35636 | 10/1997 |
| WO | WO97/47236 | 12/1997 |
| WO | WO98/26716 | 6/1998 |
| WO | WO98/29030 | 7/1998 |
| WO | 9851025 | 11/1998 |
| WO | WO 98/52641 | 11/1998 |
| WO | WO99/26530 | 6/1999 |
| WO | WO 99/34453 A1 | 7/1999 |
| WO | WO99/59460 | 11/1999 |
| WO | WO00/16686 | 3/2000 |
| WO | WO 01/51123 | 7/2001 |
| WO | WO03/068047 | 8/2003 |
| WO | WO2004/091719 | 10/2004 |
| WO | WO2006/010010 | 1/2006 |
| WO | WO2006/056857 | 6/2006 |
| WO | WO2006/069215 | 6/2006 |
| WO | WO2007/025163 | 3/2007 |
| WO | WO2007/047966 | 4/2007 |
| WO | WO2008/011570 | 1/2008 |
| WO | WO2008/011577 | 1/2008 |

OTHER PUBLICATIONS

C. Hierold et al. (Germany 1998) "Implantable Low Power Integrated Pressure Sensor System for Minimal Invasive Telemetric Patient Monitoring" IEEE pp. 568-573.

Cassereau et al. "Time Reversal of Ultrasonic Fields Part 3: Theory of the Closed TimeReversal Cavity" IEEE Transactions on Ultrasonics Ferroelectrics and Frequency Control vol. 39 No. 5, Sep. 1992 pp. 579-592.

Dipl.Ing Torsten Eggers et al. (Germany) "Implantable Telemetric Endosystem (ITES)" IMSAS Institut Fur MikrosensorenAktuatoren UndSysteme, 1998, 2 pp.

ER. Cosman et al. (Massachussetts Apr. 1979) "A Telemetric Pressure Sensor for Ventricular Shunt Systems" Surgical Neurology vol. 11, No. 4, pp. 287-294.

Fink et al. "Time Reversal Acoustics" 2004 IEEE Transactions on Ultrasonics Ferroelectrics and Frequency Control Joint 50th Anniversary Conference Ultrasonics Symposium pp. 850-859.

Fink "Time Reversal of Ultrasonic Fields Part 1: Basic Principles" IEEE Transactions on Ultrasonics Ferroelectrics and Frequency Control vol. 39 No. 5, Sep. 1992, pp. 555-566.

G. W. H. Schurink et al. (1998) "Late Endoleak after Endovascular Therapy for Abdominal Aortic Aneurysm" Eur. J. Vasc. Endovasc. Surg. vol. 17, pp. 448-450.

GH White et al. (1997) "Endoleak Following Endoluminal Repair of AAA: Management Options and Patient Outcomes" J. Endovasc Surg. p. I45.

Karl E. Richard et al. (Germany Jan. 1999) "First clinical results with a telemetric shunt-integrated ICP-sensor" Neurological Research vol. 21, pp. 117-120.

Prof. Dr. Johannes Zacheja et al. (Germany Sep. 1996) "An Implantable Microsystem for Biomedical Applications" Micro System Technologies 96 pp. 717-722.

S. K. Gupta et al. (1999) "Use of a Piezoelectric Film Sensor for Monitoring Vascular Grafts" The American Journal of Surgery vol. 160, pp. 182-186.

T. Chuter et al. (Sweden Jan. 1997) "Aneurysm Pressure following Endovascular Exclusion" Eur. J. Vasc. Endovasc. Surg. vol. 13, pp. 85-87.

T.A. Cochran et al. (1990) "Aortic Aneurysm Abdominal" Current Therapy in Adult Medicine Fourth Edition, pp. 509-517.

Wu et al. "Time Reversal of Ultrasonic Fields Part 2: Experimental Results" IEEE Transactions on Ultrasonics Ferroelectrics and Frequency Control vol. 39 No. 5, Sep. 1992, pp. 567-578.

Z. Tang et al. (May 1995) "Data Transmission from an Implantable Biotelemeter by LoadShift Keying Using Circuit Configuration Modulator" IEEE Transactions on Biomedical Engineering vol. 42 No. 5, pp. 524-528.

* cited by examiner

IMPLANTABLE MEDICAL DEVICE WITH INTEGRATED ACOUSTIC TRANSDUCER

CROSS-REFERENCE TO RELATED APPLICATIONS

This application is a continuation of U.S. patent application Ser. No. 11/287,557, filed on Nov. 23, 2005, now U.S. Pat. No. 7,580,750 which claims priority under 35 U.S.C. §119 to U.S. Provisional Patent Application Ser. No. 60/630,801, entitled "Implantable Medical Device With Integrated Acoustic Transducer," filed on Nov. 24, 2004, each of which are expressly incorporated herein by reference in their entirety for all purposes.

FIELD OF INVENTION

The present invention relates to the field of diagnostic and therapeutic medical implants and data communication between them.

BACKGROUND

Communication between diagnostic and/or therapeutic medical device implants within the body can be highly beneficial. One example is the information exchange between an implantable sensor and an implantable pulse generator (IPG), that uses the sensed information for optimizing its operation. Published U.S. Patent Application US 2004-0204744A1, which is incorporated by reference herein, discloses using an intra-body acoustic communication link for this purpose. As taught in that publication, in order to minimize energy consumption, the sensor implant is left deactivated (i.e., not powered on) until an acoustic wave pulse received from another implanted device activates the sensor implant using acoustic switch technology. Two possible transducer configurations applicable for this concept are disclosed in this published application.

Acoustic transducers integrated in implantable medical devices are known. For example, U.S. Pat. No. 6,477,406, discloses several acoustic transducer configurations used for listening to sounds produced by the heart. However, these transducers were designed only for receiving acoustic signals, and not for transmitting acoustic signals. Moreover, the transducer configurations of this patent are optimized to low sound frequencies in a range of 5-300 Hz, while for acoustic communication much higher frequencies are used, e.g., in an ultrasonic range of 20 kHz-10 MHz. In particular, U.S. Pat. No. 6,477,406 does not teach an acoustic transducer that can effectively produce ultrasonic transmission or serve as an effective receiver at high acoustic frequencies.

Acoustic communication was also suggested for data exchange between an implantable device and external unit, such as disclosed in U.S. Pat. No. 5,113,859. However, this patent also does not teach or describe an acoustic transducer capable of performing the communication, nor is there any transducer disclosed or described that is capable of transmitting ultrasonic signals at a level sufficient for activating an acoustic switch and/or communicating with a second implant.

SUMMARY

In one embodiment, an implantable medical device comprises a hermetically sealed housing having a housing wall with an interior surface. An ultrasonic acoustic transducer comprising one or more piezoelectric discs is fixed to the interior surface of the housing wall, such that the housing wall acts as a diaphragm in response to induced movement by the one or more piezoelectric material discs. The one or more piezoelectric discs may comprise, for example, a material selected from the group of materials comprising piezoelectric crystal, electro-active ceramics, ceramic-polymer composite, PVDF, and PVDF copolymer. The transducer is preferably configured to operate at a resonance frequency that is between 20-200 KHz.

In embodiments of the invention, the device further comprises an annular ring attached to the interior wall of the surface of the housing wall and surrounding the one or more discs. The device may also further include a membrane interposed between the interior wall surface and the piezoelectric discs, wherein the membrane has a substantially greater thickness than the enclosure wall. For example, in one embodiment, the membrane is mounted on a pedestal, the pedestal attached to the wall surface and having a smaller diameter than the piezoelectric discs.

In some embodiments, the interior wall may comprise an indent portion defining a recess, wherein the transducer is mounted to the wall within the recess. In some embodiments, the one or more piezoelectric discs comprise two discs, and further comprising an electrode positioned between the piezoelectric discs, wherein a respective electrical lead is coupled to each of the two discs and the electrode. An amplifier is integrated with the one or more piezoelectric discs in order to minimize parasitic effects and noises.

In some embodiments, the one or more transducer discs may comprise a single disc attached about an outer circumference of the disc to a support structure, the support structure attached to the enclosure wall surface and elevating the transducer disc from the wall so as to allow the disc to flex into a space defined between the disc and the enclosure wall. The support structure may comprise, for example, a membrane interposed between the interior wall surface and the piezoelectric disc. In such embodiments, the membrane may be mounted on a pedestal, the pedestal attached to the wall surface, wherein the pedestal has a smaller diameter than does the piezoelectric disc. In embodiments of the invention, the transducer may be a flexural type or a flex-tension type acoustic transducer.

In accordance with a further embodiment of the invention, an implantable medical device comprises a hermetically sealed housing having at least one hermetic electrical feed through. An acoustic lead is provided, the acoustic lead having a proximal end connected to the electrical feed through, and a distal end configured for transmitting and receiving acoustic signals. The acoustic lead includes an ultrasonic acoustic transducer comprising one or more piezoelectric discs. In various embodiments, the transducer may be coupled to a distal portion of the acoustic lead, or alternatively, to a proximal portion of the acoustic lead. For example, the transducer may be coupled to a proximal portion of the lead, wherein the distal portion of the lead comprises a wave guide.

The device may further comprise means for anchoring the acoustic lead to a location in a body lumen. For example, the means for fixing the lead comprising one or more items selected from the group comprising a radial anchor, a hook, a screw, and an elastic band. In one embodiment, the device further comprises an electrical lead coupled to the housing, wherein the acoustic lead is fixed to the electrical lead.

BRIEF DESCRIPTION OF THE DRAWINGS

The drawings illustrate the design and utility of embodiments of the invention, in which similar elements are referred to by common reference numerals. With the understanding that these drawings depict only exemplary embodiments of the invention, and are not therefore to be considered limiting its scope, the embodiments will be described and explained with additional specificity and detail through the use of the accompanying drawings, in which.

DETAILED DESCRIPTION OF THE ILLUSTRATED EMBODIMENTS

The present invention is directed to an (active) implantable medical device such as a pacemaker, implantable cardioverter defibrillator (ICD), Cardiac Rhythm Therapy (CRT), a standalone hemodynamic monitor, or implantable drug pump, which communicates with another implanted device (not shown), or an extracorporeal device (not shown), using an acoustic communication link. Towards this end, the active implantable device is provided with an acoustic transducer capable of transmitting an acoustic pulse sufficient for activating an acoustic switch in the receiving device, such as described in U.S. Pat. No. 6,628,989. For this purpose, an acoustic pulse that is at least 0.1 msec wide, and at least a 50 Pa peak pressure is preferred. For example, a pulse of 0.5 msec and 500 Pa may be used in one embodiment. The acoustic transducer is preferably capable of transmitting acoustic pulses at a pressure of at least 0.05 Pa (measured at 20 cm in vitro) and receiving signals of 0.05 Pa. The frequency range at which the system can operate is preferably within a range of 20 KHz-3 MHz. In order to maximize the efficiency of the transducer, it is preferably designed to operate at its resonance frequency.

Figure 1A:
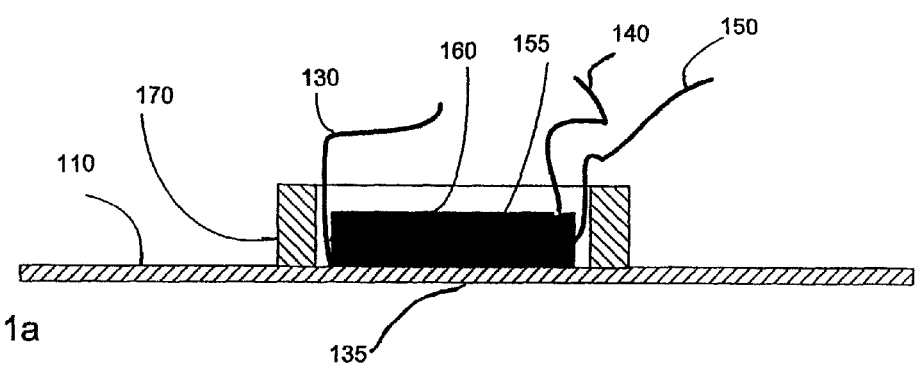
FIGS. 1a-1d depict embodiments of an exemplary acoustic transducer constructed on an internal housing surface of an active medical implant device, such as an IPG or a drug pump.

In one embodiment, the acoustic transducer is constructed on an internal surface of the implantable device housing, typically a hermetically sealed enclosure, with a portion of the enclosure housing wall coupled to the transducer and acting as a vibrating diaphragm. FIG. 1a discloses one such acoustic transducer, in which a pair of piezoelectric discs 160 are coupled to an internal flat surface of a hermetic implant enclosure wall 110, wherein the portion 135 of the wall 110 to which the transducer discs 160 are attached acts as a vibrating diaphragm.

Piezoelectric materials are well known and the proposed design of the transducer can use any material from the group including: electrostrictive ceramic, piezoelectric ceramic, piezoelectric ceramic-polymer composite and piezoelectric polymers. The proposed design can employ one or more piezoelectric discs with an electrode there between discs. For example, transducer 160 has two discs surrounding an electrode 155. This structure allows for electrical connection of the piezoelectric discs in series, in parallel, or in a combination of the two, using electrical contacts to the disc electrodes. Three respective leads 130, 140 and 150 are provided for this purpose, which allows for optimization of the transducer 160 for performing specific tasks.

The voltage available in an IPG is usually relatively low, produced from its internal 2-3 volt battery. For transmitting an acoustic signal required for activating an acoustic switch, a relatively high voltage may be required (for example, several hundred volts). Using multiple, thin discs of piezoelectric material connected in parallel will produce the equivalent acoustic power of a single, thicker disc, but at a substantially lower voltage. For example, two piezoelectric discs that are each 0.5 mm thick, connected in parallel, will produce a similar acoustic power as a 1 mm thick piezoelectric disc at half the voltage. However, if one wishes to optimize the receiving sensitivity of the transducer, serial connection of the thin piezoelectric discs will result in a higher voltage signal per a given acoustic signal, than a single thick disk. The ceramics may also be connected anti-parallel, to produce a bending moment as a piezoelectric bimorph.

For producing the transmitted acoustic signal, the proposed acoustic transducer should be efficient and durable. Preferably, the transducers should work at their resonance frequency in order to optimize the efficiency and sensitivity of the transducer. The acoustic transducer of FIG. 1a belongs to a family known as flexural transducers. Its resonance frequency depends on several parameters, including the type, thickness and diameter of the piezoelectric material 160, the material and thickness of the diaphragm 135, and the material, diameter, thickness, and height of a rigid ring 170 attached to the wall surface 110 surrounding the transducer and defining the diaphragm 135. For example, an acoustic transducer with the following parameters will have a resonance frequency of about 40 KHz: piezoelectric ceramic discs (160) that are 1 mm thick and 10 mm diameter; titanium diaphragm (135) that is 1 mm thick and 13 mm in diameter; and a surrounding titanium ring (170) of at least 1 mm in height with an outer diameter of 20 mm. Changing the resonance frequency can be done by modifying the various parameters as will be appreciated by those skilled in the art of acoustic transducer design.

The piezoelectric discs 160 can be coupled to the diaphragm by various known methods including using an adhesive, an electrically conductive adhesive, gel or liquid coupling, or by a direct fabrication of the piezoelectric material 160 on the diaphragm 135. In FIG. 1a, the diaphragm 135 is part of a hermetic enclosure wall 110, with its vibrational modes defined by its thickness and by the material and dimensions of the concentric rigid ring 170 attached to it. The ring 170 can be attached to the diaphragm using, for example, welding, brazing, diffusion bonding, adhesive or machining.

Figure 1B:
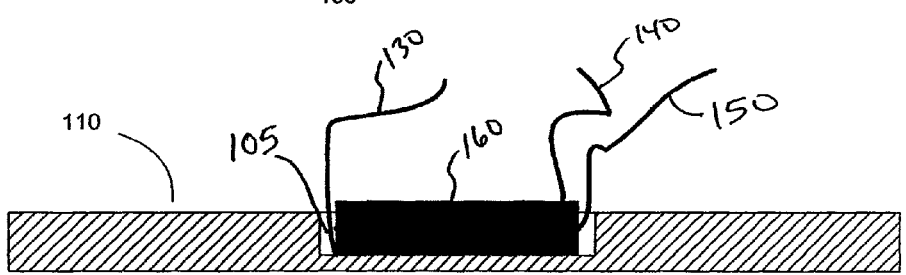
Figure 1C:
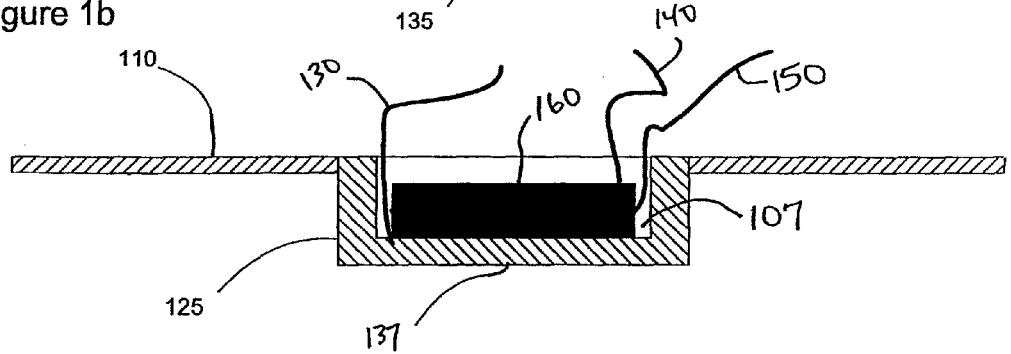
Figure 1D:
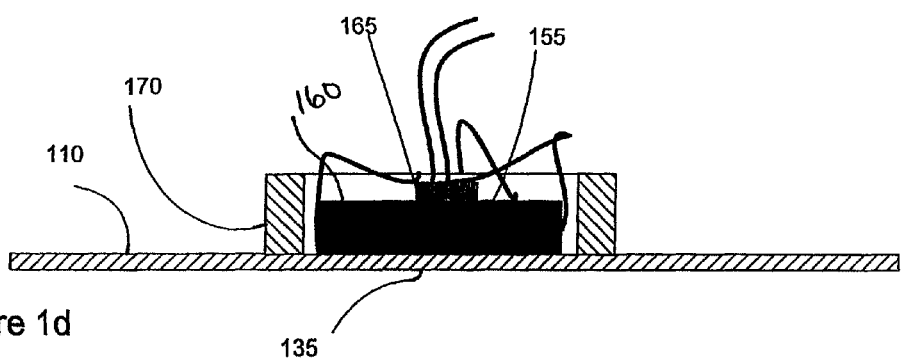

An alternate configuration (shown in FIG. 1b) is achieved by forming a groove 105 in the enclosure wall 110, and attaching the piezoelectric discs 160 to a very thin diaphragm portion 135 of the wall, i.e., within the grove. This embodiment is more suitable where the enclosure wall 110 is relatively thick. Another alternative, (shown in FIG. 1c) is to produce an indent 107 in the wall 110 by stamping or coining, or by attachment of a separate diaphragm member 137, including a concentric ring portion 125. The parts can be attached by any conventional method, such as, e.g., welding, brazing, diffusion bonding, adhesive or machining. For optimizing the receiving sensitivity of the transducer, a separate disc of a piezoelectric material with high acoustic sensitivity can be used, such as a layer of PVDF, attached to the piezoelectric ceramic discs 160 used for transmission. Another way to improve the receiving signal to noise is by integrating an amplifier 165 to the disc structure 160 (shown in FIG. 1*d*), in order to minimize parasitic effects and noises. It will be appreciated that the addition of the amplifier shown in FIG. 1*d* may be equally applicable to the other embodiments disclosed and described herein.

In an alternate embodiment, a transducer whose properties are substantially independent of the enclosure wall is preferred. Various IPGs and other active medical devices may have different enclosure material, thickness and thermal treatment as well as tolerances on each of these parameters. The resonance frequency and as a result the performance of a transducer that uses the wall of the enclosure as a diaphragm may vary significantly due to these changes, or the wall properties may be unsuited to yield the desired transducer properties.

For these reasons it is advantageous to have a transducer in which the acoustic performance is governed by the transducer structure detached from the enclosure wall. An example of such a design is given in FIG. 2*a*, in which the piezoelectric discs 160 are mounted on a separate membrane, that is itself mounted to the enclosure wall surface 110. In the illustrated embodiment, the membrane 132 may be metallic and has an integrally formed annular ring portion 120 that surrounds the piezoelectric discs 160 in a manner similar to ring 170 in the embodiments of FIGS. 1*a* and 1*d*.

For example, in an IPG, the enclosure wall is usually made of titanium, with a wall thickness of about 0.125 mm-0.5 mm. On the other hand, the metallic membrane 132 and the piezoelectric ceramic discs are preferably each about 1 mm thick, i.e. such that the influence of the relatively thin enclosure wall 110 on the performance of transducer is substantially small. Other thickness and diameters of materials can be used as will be apparent to those skilled in the art of designing acoustic transducers.

Figure 2A:
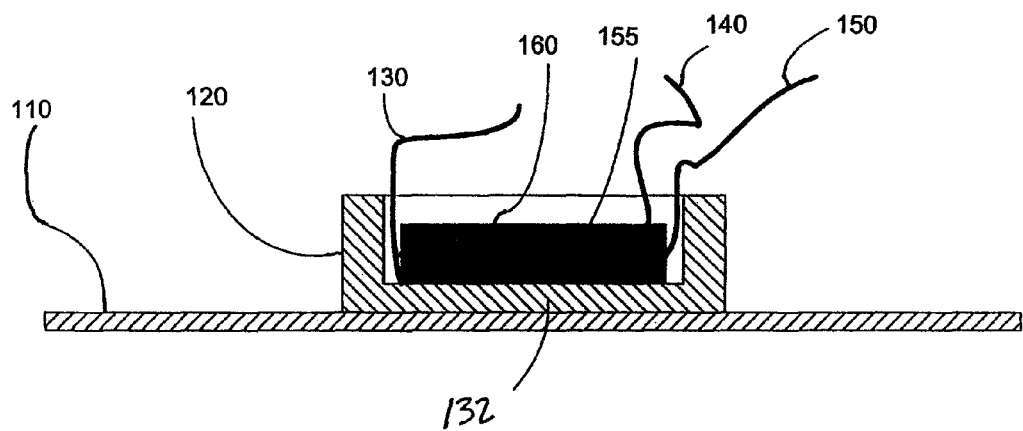
FIGS. 2a-2b and 3a-3c depict alternate acoustic transducer designs coupled to an internal housing surface of an active medical implant device.
Figure 2B:
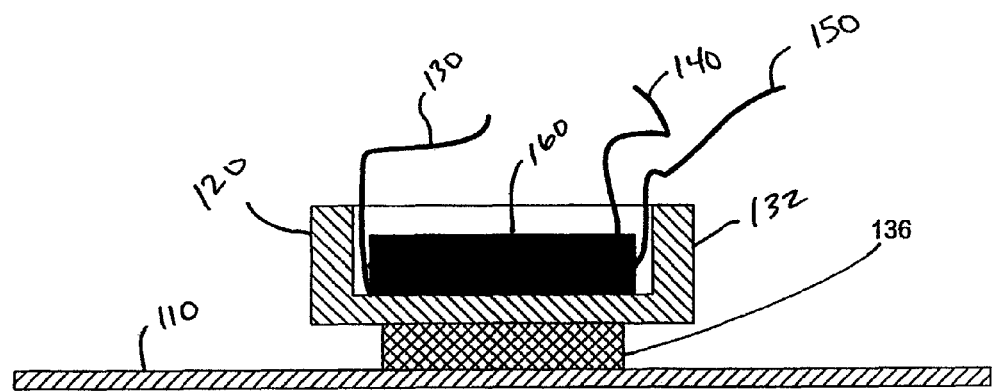

FIG. 2*b* depicts a variation of the embodiment of FIG. 2*a*. The natural mode of vibration of a transducer surface may include areas which vibrate in opposite directions, which may harm the acoustic performance. It is possible to optimize the motion transferred to the metallic casing by mounting the transducer on a pedestal 136, such that only surfaces which move together are coupled to the enclosure wall 110. For example, in FIG. 2*b*, the membrane enclosure 132 (including therein the transducer discs 160) is coupled to the enclosure wall 110 by a metallic or polymeric material disc 136, whose diameter is less than that of the transducer disc(s). In such configuration, only the motion of the center portion of the transducer couples to the wall 110 and to the acoustic medium, while the motion of the edge, which may be of opposite polarity, is not. As will be apparent, other methods of attachment can be designed to fit to specific transducer and enclosure structures.

Figure 3A:
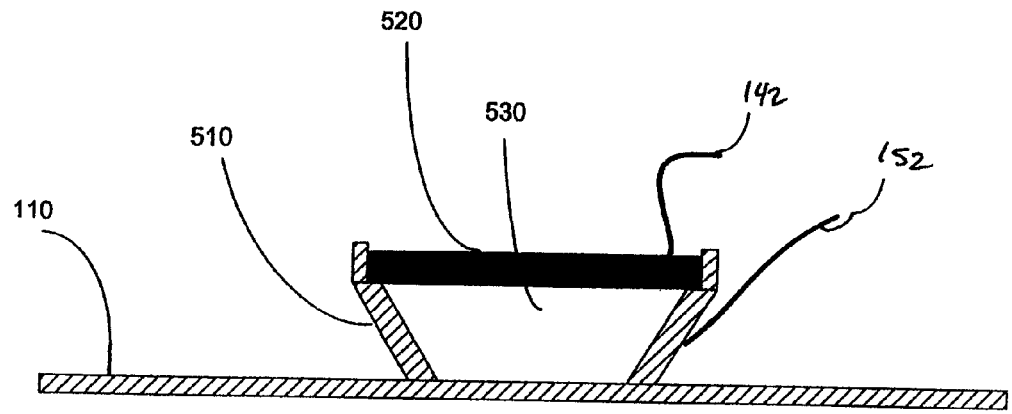
Figure 3B:
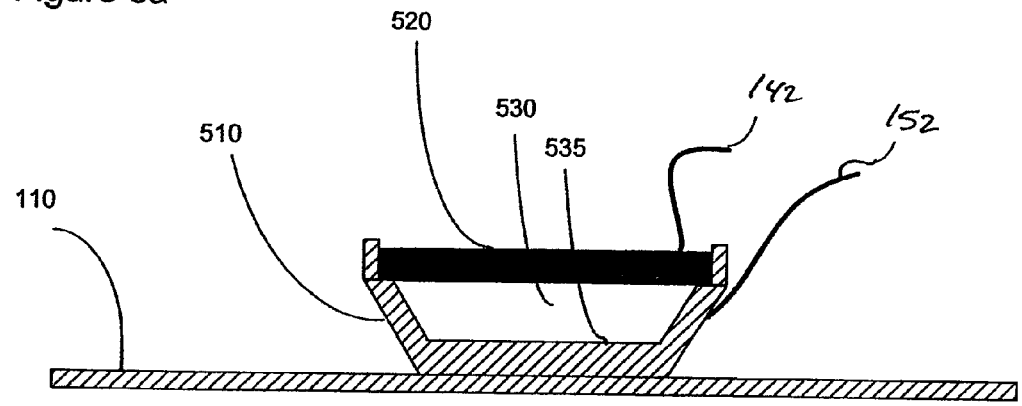
Figure 3C:
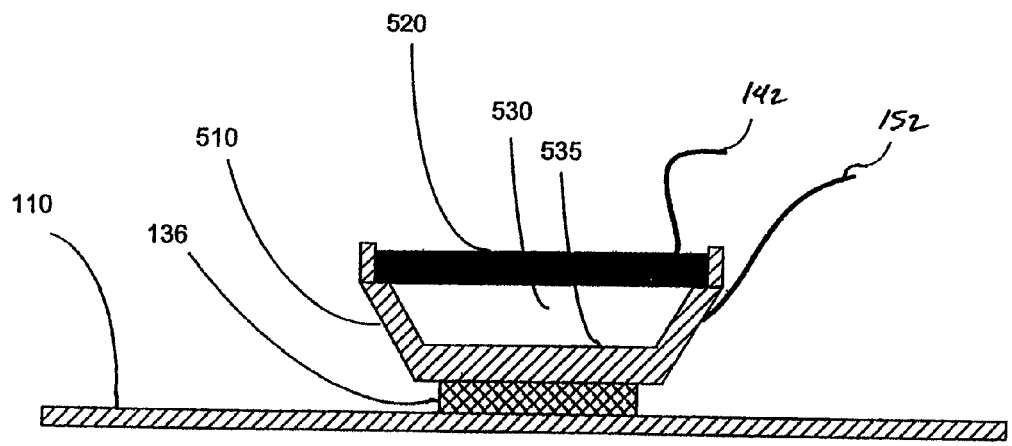

Another family of transducers that can be useful for embodiments of the invention is shown in FIGS. 3*a*-3*c*, and is known as a "flex-tensional" transducer. This device is based upon the principles of the flextensional actuator design. Specifically, an actuator having an electro-active substrate 520 is used, the actuator having at least one and preferably a pair of planar or domed surfaces driving end caps. The use of flextensional principles provides significant improvements in implantable output actuators as the available space in the implantable device enclosure is limited. The use of the inventive output actuator described herein allows for movement of a piezo to translate into a proportionally larger movement of the flextensional actuator.

The lever action of the end caps in the flextensional devices also decreases the effective impedance of the piezo to match optimally the impedance of the body part being driven. Two configurations are presented, one (shown in FIG. 3*a*) in which the transducer 520 is attached about an outer circumference of the disc 520 to a support structure 510, the support structure 510 being attached to the enclosure wall surface 110 and elevating the transducer disc 520 there from, so as to allow the disc 520 to flex into a space 530 defined between the disc 520 and the enclosure wall 110. A pair of electrical leads are provided, one (142) coupled to the transducer disc 520, and the other (152) to the support structure 510. A second configuration design (shown in FIG. 3*b*) is where an additional metallic membrane 535 is provided for attaching the support structure 510 to the enclosure wall 110, the membrane 520 being substantially stiffer than the enclosure wall 110, thereby minimizing the influence of the wall 110 on the performance of transducer. The embodiment of FIG. 3*c* incorporates the features of both FIGS. 2*b* and 3*b*, wherein the metallic membrane 535 is itself mounted to a metallic center pedestal 136.

The embodiments described above use several transducer configurations, however other transducer configurations and/or variations and/or modifications of the concepts herein taught may appear to those skilled in the pertinent art. Integrating the acoustic transducer within the medical device enclosure is practically transparent to the implanting physician. Also in this configuration the hermetic enclosure protects the transducer and its electronics from the environment. However, usually the implantation location of the active medical device is limited due to its size and the wish to minimize the implantation procedure invasiveness. As a result the implantation site can be sub-optimal for acoustic communication. For example, an IPG is most often implanted under the skin beneath the collar bone. Due to anatomy and the physical fact that acoustic waves can not cross the lungs, any communication between the IPG and a second implant located within the heart may be sub-optimal.

Figure 4:
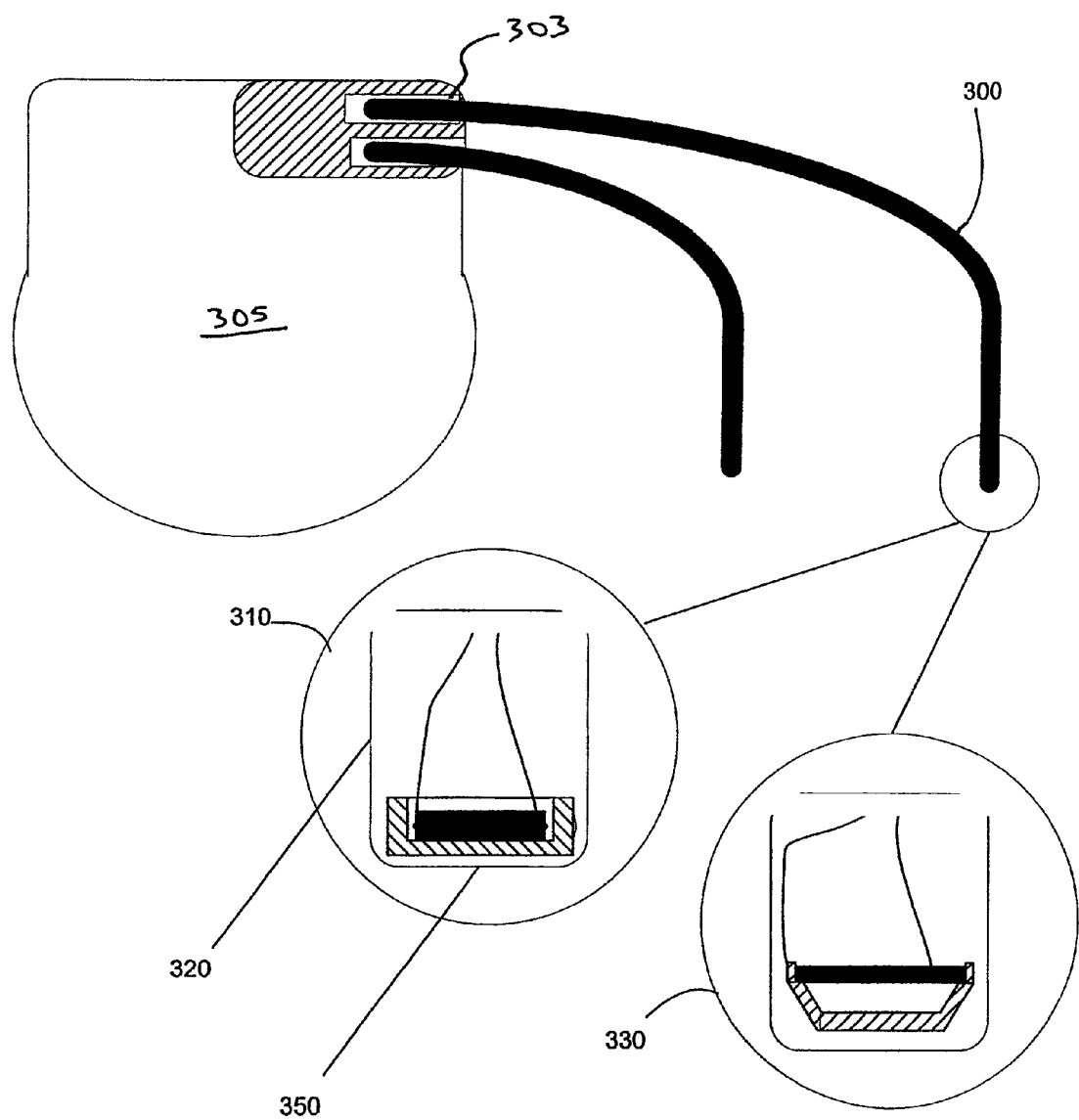
FIG. 4 depicts exemplary configurations of an acoustic transducer integrated on an end of an implantable acoustic lead, whereby the line-of-sight of the transducer(s) may be optimized relative to the location of a second implant.

FIG. 4 illustrates another embodiment of the invention, in which the linkage between the location of the IPG 305 and that of the transducer is disconnected. As shown in FIG. 4, an acoustic transducer, alternately 320 or 330, may be located at the tip of a lead 300, referred to herein as an "acoustic lead." The acoustic lead 300 can be similar to an electrical lead commonly used in IPGs (e.g., for pacing). In a preferred embodiment, the acoustic lead 300 is not positioned within the heart, but rather in a vein leading to the right atrium, e.g. the subclavian vein, the cephalic vein, the right or left brachiocephalic vein, the superior or inferior vena cava or the internal jugular vein. The connection of the said acoustic lead 300 to the IPG 305 can be via a standard electrical hermetic feed through 303 of the IPG 305.

Implantation of the acoustic lead 300 can be performed using the same catheterization techniques used for implanting IPG electrical leads. However, instead of entering the right atrium (and in some cases the heart right ventricle), the acoustic lead can preferably be located external to the heart, and preferably in a location with a direct "line of sight" between the lead acoustic source and the second implant. Many of the risks involved in implanting an IPG electrical lead, such as thrombus formation or damage to the heat valve, may be avoided by not entering the heart or passing through the heart valve. The fixation of the acoustic lead 300 may be accomplished, for example, by a radial anchoring of the device to a wall of the vessel using a stent-like device, or with a screw or hook-type fixation to the vessel wall.

Figure 6:
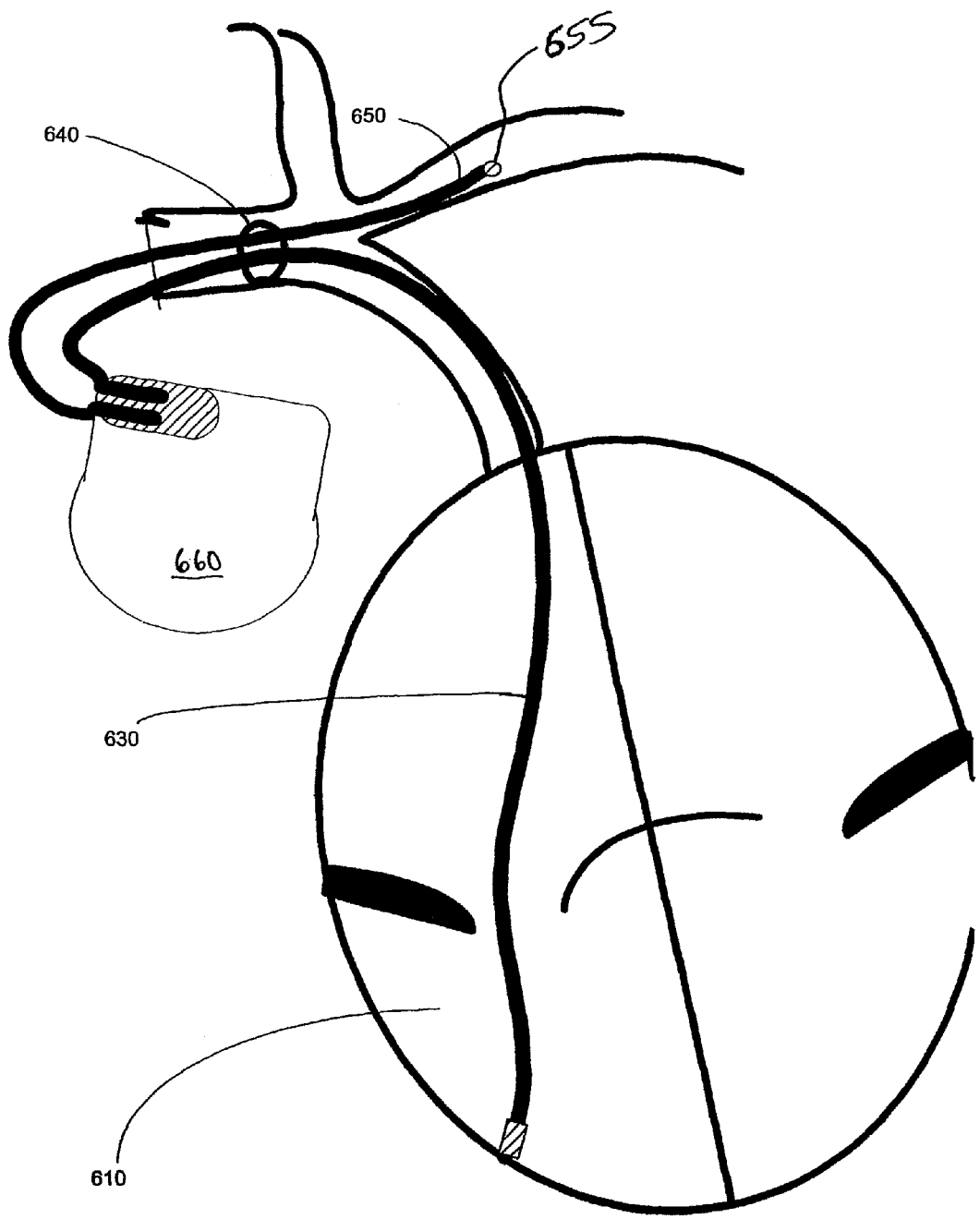
FIG. 6 depicts a further alternate configuration in which an acoustic lead is fixed to another lead using an elastic band.

Alternatively, an acoustic lead can be fixed to another lead using, for example, an elastic band 640, as shown in FIG. 6. In this configuration, a first electrical lead 630 extending from an IPG 660 is implanted (for example) for pacing in the patient's right ventricle 610. A guide wire, and preferably a catheter, are threaded into an elastic band 640 attached on or around the first electrical lead 630. An acoustic lead 650 may then be implanted over the wire or the catheter. This proposed procedure should be considered only as an example, and other techniques and methods of implanting and fixating an acoustic lead will be apparent to those skilled in the art.

An acoustic transducer 655 is integrated at the tip of the acoustic lead 630, and can be of any type of transducer. For example, FIG. 4 shows the exemplary use of two designs discussed previously, a flexural configuration 310, and a flextensional design 330. Preferably the transducer electrical contacts and leads to the IPG are isolated from body fluids. Since the impedance of the transducer will be similar in magnitude to the impedance of the IPG leads (on the order of several hundreds of ohms), the same isolation techniques used for standard IPG leads can also be used for the acoustic lead. Also, the diaphragm of the transducer 350 can be coated with the same polymeric material of the lead, e.g. polyurethane or silicone. However, care should be taken that gas bubbles will not be preserved in this layer, so as not to attenuate the acoustic wave transmission.

Figure 5:
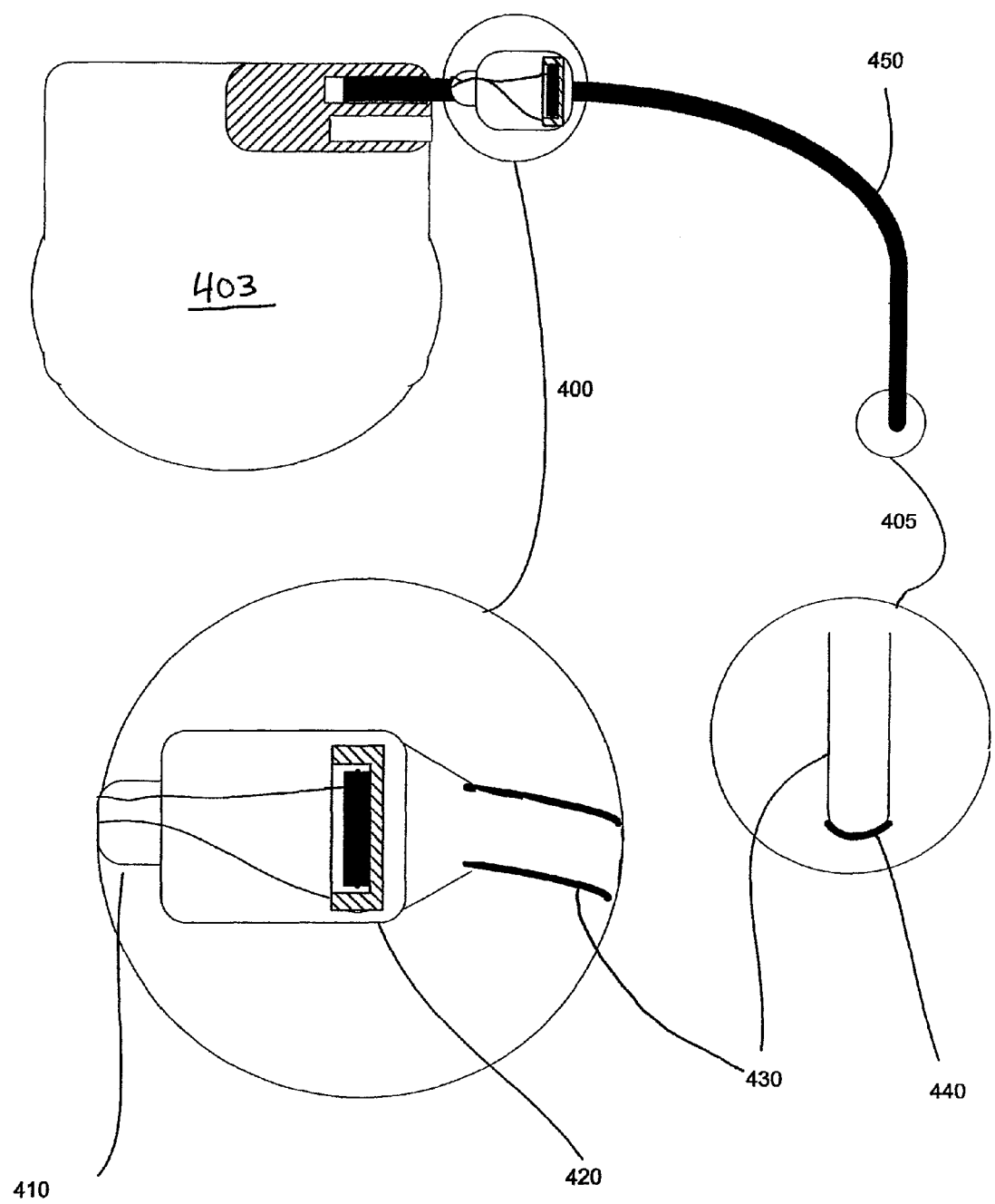
FIG. 5 depicts an alternate configuration of an acoustic lead, in which acoustic waves are transmitted (or received) at a distal end of a lead tube serving as a wave guide, and in which the acoustic transducer is located close to (or within) an active medical implant device and coupled to the lead tube.

Another embodiment, including another acoustic lead configuration, is shown in FIG. 5. In this embodiment, the acoustic lead is based on an acoustic wave-guide 450 coupled on one end to an acoustic transducer 400. In this configuration, the acoustic waves propagate along, and exit on a far end 405 of, the wave guide 450. The acoustic transducer can be external to the IPG (as shown in FIG. 5), or integrated within the IPG enclosure (not shown). Preferably a funnel shaped structure or a gradual change of the material properties through which the sound waves propagate (420 to 430) is used to optimize the coupling of the transducer to the wave-guide by matching their mechanical impedances. This configuration allows the usage of a larger transducer for producing the acoustic waves, while still directing the acoustic energy to an optimized location, using a small size, catheterization compatible wave-guide. Again, the transducer can be of any desired type and configuration.

The design of the wave-guide 450 should ensure that a substantial part of the acoustic energy produced by the acoustic transducer module 400 will be emitted at the lead far end 405. The material of which the wave-guide is preferably made of, or filled with, a good acoustic conductor. Liquids, including water and saline, or polymers, such as polyurethane, nylon, or rubber, can be used for this purpose. The wall 430 of the lead 450 should serve as a reflector for the acoustic waves to prevent leakage of the acoustic energy out of the wave-guide. The wall 430 can be made of a substantially rigid material such as a metal tube, or a polymer tube radially reinforced with metal or glass fibers.

Alternatively, the waveguide 450 may consist of a flexible metal tube or wire, which conducts the acoustic vibrations via longitudinal waves. Such metal wire or tube may be encased in a thin solid or gas-containing cladding, which insulates it mechanically from the surrounding fluid. The far end of the wave-guide 405 serves as an acoustic wave source acoustically coupled to the body. For example, a thin membrane 440, e.g., made of a polymer or a metal, may serve as the acoustic diaphragm. This acoustic membrane 440 may be resonant at the desired frequency of operation, in order to increase its effectiveness as an acoustic radiator. Alternately, the far end of the lead may contain a resonant structure, such as a mechanical structure or a Helmholtz resonator, coupled to the membrane 440.

All the above-disclosed, implantable transducers can, in addition to activation and communication with a second implant, also be used for acoustically energizing and charging the second implant. Preferably, the acoustic lead designs of FIGS. 4 and 5 should be used for this purpose, taking advantage of the optimized location of the transducer in these configurations relative to the second implant. The possible line of sight between the lead transducer and the second implant, combined with the possible small distance between them, which can be between a few millimeters to several centimeters, can significantly reduce the required energy for charging the second implant battery or capacitor. The charging can be done using energy from the IPG battery, or from an extracorporeal power source (either telemetrically, or by making a small incision at the IPG implantation site), disengaging the acoustic lead from the IPG controller, connecting the acoustic lead to an external power source, and using the acoustic energy produced by the acoustic lead to charge the battery within the second implant.

Preferably, the battery capacity of the second implant is such that charging will be not be required for a duration longer than that of the IPG battery. Upon the replacement of the IPG controller, the acoustic lead can be connected to an external power source for charging the second implant battery. Alternatively, an acoustic catheter can be used for acoustically charging the second implant. This catheter can be built similar to the acoustic lead, with an acoustic transducer at its tip or by serving as an acoustic wave-guide. The acoustic catheter can be introduced to the body in a similar technique used for right heart catheterization. This procedure is usually carried out via the femoral vein and internal jugular subclavian vein, using a standard guide wire based catheterization or by a floating balloon (e.g., a Swan-Ganz catheter). The procedure can be guided using fluoroscopy or pressure pattern measurements. Since the acoustic source on the catheter can be located very close to the second implant, the charging process is preferably very efficient and local.

What is claimed is:

1. An implantable medical device adapted to be acoustically coupled to a second medical device, the implantable medical device comprising:
   a hermetically sealed implantable device housing having a housing wall with an interior surface;
   an ultrasonic transducer disposed within the implantable device housing and configured to acoustically couple to the second medical device, the ultrasonic transducer comprising a piezoelectric disc configured to transmit an outgoing acoustic signal to the second medical device and receive an incoming acoustic signal from the second medical device;
   a metallic membrane interposed between the interior surface of the housing wall and the piezoelectric disc, the membrane configured to couple a center portion of the piezoelectric disc to the interior surface of the housing wall, the metallic membrane including an annular ring portion radially surrounding the piezoelectric disc; and
   wherein the ultrasonic transducer is configured to operate at a resonance frequency at or above 20 KHz.

2. The device of claim 1, wherein the piezoelectric disc comprise two discs, and further including an electrode positioned between the piezoelectric discs.

3. The device of claim 2, further including a respective electrical lead coupled to each of the two piezoelectric discs and the electrode.

4. The device of claim 1, further including an amplifier integrated with the piezoelectric disc, the amplifier configured to minimize parasitic effects and noise in the incoming acoustic signal received from the second medical device.

5. The device of claim 1, wherein the membrane has a substantially greater thickness than a thickness of the housing wall.

6. The device of claim 5, wherein the membrane is mounted on a pedestal, the pedestal attached to the interior surface of the housing wall, the pedestal having a smaller diameter than each of the one or more piezoelectric discs.

7. The device of claim 1, wherein the second medical device is an implantable device.

8. The device of claim 1, wherein the second medical device is an extracorporeal device.

9. The device of claim 1, wherein the implantable medical device is an implantable pulse generator.

10. An implantable medical device adapted to be acoustically coupled to a second medical device, the implantable medical device comprising:
   a hermetically sealed implantable device housing having a housing wall with an interior surface;
   an ultrasonic transducer disposed within the implantable device housing and configured to acoustically couple to the second medical device, the ultrasonic transducer including one or more piezoelectric discs configured to transmit an outgoing acoustic signal to the second medical device and receive an incoming acoustic signal from the second medical device;
   a metallic membrane interposed between and in contact with the interior surface of the housing wall and the ultrasonic transducer, the metallic membrane including an annular ring portion radially surrounding the one or more piezoelectric discs; and
   wherein the ultrasonic transducer is configured to operate at a resonance frequency at or above 20 KHz.

11. The device of claim 10, wherein the one or more piezoelectric discs comprise two piezoelectric discs, and further including an electrode positioned between the piezoelectric discs.

12. The device of claim 11, further including a respective electrical lead coupled to each of the two piezoelectric discs and the electrode.

13. The device of claim 10, further including an amplifier integrated with the one or more piezoelectric discs, the amplifier configured to minimize parasitic effects and noise in the incoming acoustic signal received from the second medical device.

14. The device of claim 10, wherein the annular ring is attached to the interior surface of the housing wall.

15. The device of claim 10, wherein the membrane has a substantially greater thickness than a thickness of the housing wall.

16. The device of claim 10, wherein the second medical device is an implantable device.

17. The device of claim 10, wherein the second medical device is an extracorporeal device.

18. The device of claim 10, wherein the implantable medical device is an implantable pulse generator.

19. An implantable medical device adapted to be acoustically coupled to a remote device implanted within the body, the implantable medical device comprising:
   a hermetically sealed implantable device housing having a housing wall with an interior surface;
   an ultrasonic transducer disposed within the implantable device housing and configured to acoustically couple to the remote device, the ultrasonic transducer configured to transmit an outgoing acoustic signal to the remote device at a frequency at or above 20 KHz; and
   a metallic membrane interposed between and in contact with the interior surface of the housing wall and the piezoelectric disc, the membrane configured to couple a center portion of the piezoelectric disc to the interior surface of the housing wall, the metallic membrane including an annular ring portion radially surrounding the ultrasonic transducer.

* * * * *